(12) United States Patent
Nguyen-Dinh et al.

(10) Patent No.: US 6,645,148 B2
(45) Date of Patent: Nov. 11, 2003

(54) ULTRASONIC PROBE INCLUDING POINTING DEVICES FOR REMOTELY CONTROLLING FUNCTIONS OF AN ASSOCIATED IMAGING SYSTEM

(75) Inventors: An Nguyen-Dinh, Valleres (FR); Aimé Flesch, Andrésy (FR)

(73) Assignee: Vermon, Tours Cedex (FR)

( * ) Notice: Subject to any disclaimer, the term of this patent is extended or adjusted under 35 U.S.C. 154(b) by 53 days.

(21) Appl. No.: 09/811,147

(22) Filed: Mar. 20, 2001

(65) Prior Publication Data

US 2002/0138007 A1 Sep. 26, 2002

(51) Int. Cl.[7] .................................................. A61B 8/14
(52) U.S. Cl. ...................................... 600/459; 600/462
(58) Field of Search ................................. 600/459, 462, 600/463–465

(56) References Cited

U.S. PATENT DOCUMENTS

| | | | |
|---|---|---|---|
| 5,295,485 A | | 3/1994 | Shinomura et al. |
| 5,323,767 A | * | 6/1994 | Lafferty et al. ............. 600/109 |
| 5,351,692 A | * | 10/1994 | Dow et al. .................. 600/459 |
| 5,722,412 A | | 3/1998 | Pflugrath et al. |
| 5,738,099 A | * | 4/1998 | Chang ........................ 600/437 |
| 5,758,649 A | * | 6/1998 | Iwashita et al. ............ 600/459 |
| 6,135,958 A | | 10/2000 | Mikula-Curtis et al. |

FOREIGN PATENT DOCUMENTS

| | | | |
|---|---|---|---|
| EP | 139574 | * | 5/1985 |
| JP | 9-56716 | * | 3/1997 |

* cited by examiner

Primary Examiner—John A. Jeffery
(74) Attorney, Agent, or Firm—Larson & Taylor, PLC

(57) ABSTRACT

An ultrasonic probe is provided for use in medical diagnostic applications. The probe includes one or more ultrasonic transducers disposed in an external housing and a plurality of cables disposed in a common sheath. A pointing device, such as a trackball, rocking-key device or the like, is mounted on the probe housing for controlling a plurality of functions of a remote imaging system associated with the probe.

22 Claims, 2 Drawing Sheets

ULTRASONIC PROBE INCLUDING POINTING DEVICES FOR REMOTELY CONTROLLING FUNCTIONS OF AN ASSOCIATED IMAGING SYSTEM

BACKGROUND OF THE INVENTION

1. Field of the Invention

The present invention relates to ultrasonic probes used for diagnostic applications, and more particularly, for human body imaging.

2. Related Art

Diagnosing human organs using ultrasound is a well known procedure. Ultrasonic probes are used which employ ultrasonic transducers, with ultrasonic waves being directed from the transducer surface so as to travel through biologic structures under examination. Reflections are obtained each time the ultrasonic waves encounter impedance variation interfaces. As a result, returned echoes are received and processed by the imaging system. Summing all scanning lines received from the transducer provides an image, and the number of scanning lines and the depth of examination govern the scanning rate. Generally speaking, standard ultrasonic probes use a one dimensional (1D) transducer wherein the transducer elements are linearly arranged and no scanning control is implemented in the elevation direction. However, in some probe configurations, multi-dimensional probes (1.5D or 2D) are provided, and the transducer elements are thus arranged in a matrix so as to provide 3D steering capabilities.

Conventionally, ultrasonic probes are connected to a mainframe which is responsible for the processing of electrical signals produced by the probe transducer. The system performs an image capture or rendering operation using data from the region being scanned, and the images so obtained are produced by the synthesizing of information based on a number of different parameters, e.g., the transducer geometry, the number of scanning lines, the depth of examination and the transducer frequency. In common practice, the mainframes are provided with large advanced image settings to produce a diagnosing scan in conformance with the organ structure being examined. Typically, by using a trackball or sensitive pad of an associated keyboard, the imaging system enables a user to access most of the controls for scanning characteristics such as the frame rate, number of focal points, depth, and angle aperture, as well as other settings regarding the mode of scanning, including, e.g., CFM (color flow mapping), B-Mode, C-Mode, CW (continuous wave) and PW (pulsed wave) Doppler and the like, whereas other controls such as master gain, TGC (Time Gain Control), dynamic range, freeze, and measuring tools (for distance, surface, volume and the like) are often provided through activation of direct control buttons or by using cursors for rapid access. Given the complexity of image controls and the close attention that is required in making medical a diagnosis, ultrasonic scanning of this kind can, in practice, be a very difficult task.

Considering further prior art of interest, U.S. Pat. No. 5,295,485 to Shinimura and U.S. Pat. No. 5,722,412 to Pflugrath both disclose a handheld device which includes, in the same casing, a transducer array, ASICs (Application Specific Integrated Circuit) or conventional signal processing circuits and a display monitor. The device is battery powered and thus can be used at any desired location. However, integration of all of the various components necessary to the image processing operation results in an apparatus which is heavy and has a reduced lifetime. Further, advanced image processing functionalities like those available in conventional mainframe-based systems cannot always be implemented so that only preliminary diagnostic procedures can be carried out with such prior art devices in attempting to determine the appropriate medical intervention needed by the patient. Accordingly, these devices are essentially dedicated to emergency use where portability and autonomy is required.

In U.S. Pat. No. 6,135,958 to Mikula-Curtis, an ultrasonic scanner is equipped with a remote user interface, including a touch-pad pointing device, so the interface can be placed closer to the user and further away from the ultrasound machine. Such equipment raises the level of comfort in operation the equipment but the use of both hands is still mandatory.

SUMMARY OF THE INVENTION

In accordance with the invention, in order to overcome the drawbacks of prior art devices discussed above, there is provided an ultrasonic probe that includes a pointing device mounted on the probe casing or housing so as to enable a user to remotely control the basic functions of the associated imaging system. This pointing device is, in essence, an extension of the original setting controls provided by the system keyboard, so that a user can, at his or her option, either access the major image settings from the remote pointing device or access all of the functions of the system using the system keyboard, the two system interfaces being operable in parallel.

The probe and associated imaging system of the present invention reflect a new approach to operating ultrasonic apparatus. Unlike the conventional systems described above wherein the scanning probe and control interface are separate units and a user must manipulate the ultrasonic instrument with both hands (one for moving and steering the acoustic wave and the other for controlling the image features) and unlike a handheld scanner wherein severe compromises must be made to provide a compact volume at the detriment of image quality, the present apparatus provides a user with an imaging system which comprises at least one ultrasonic probe equipped with a limited remote user interface so that the usual functions of the imaging system can be controlled from probe, thereby significantly improving the comfort level of one using the probe during an examination.

In one embodiment of the invention, the user interface comprises a pointing device located on the probe casing, and the pointing device is a commercially available device as that used in a Notebook computer or in Gamepads or the like. Advantageously, the pointing device is located on a main face of the casing or the housing where there is more room to operate the device and easy access may be had to the device. In connecting the pointing device to the imaging system, a number of suitable techniques can be used including such as single connecting wires or an IR (infrared) line. Of course, there are a wide variety of commercially available pointing devices, and the present invention can employ most, if not all of these, including, in accordance with preferred embodiments of the invention: a sensitive pad controlled by directional actions, a rocking key pointer device, scrolling devices, a track-ball or the like. Among the important manufacturers of these devices are Fujitsu, Techtronics, and InSolutions Corp.

An important advantage of the present invention is the improvement provided thereby in working condition of the sonographers as well as in patient comfort, afforded by putting control of the basic settings of the system at the ready disposition of the user of the probe so as to permit him or her to deal better with the patient. Additional features of the invention include the provision of a one-touch image storage and of a control capability for other optional equipment (e.g., a therapy system or drug delivery functions).

Further features and advantages of the present invention will be set forth in, or apparent from, the detailed description of preferred embodiments thereof which follows.

DESCRIPTION OF THE PREFERRED EMBODIMENTS

Figure 1:
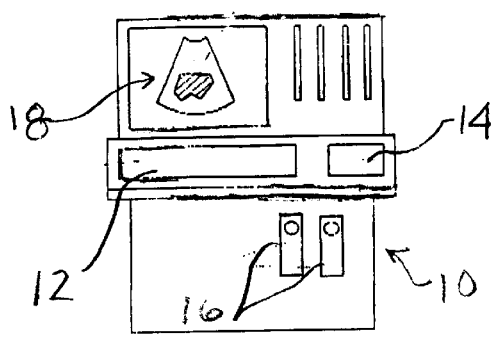
FIG. 1 is a schematic front elevational view of a prior art ultrasonic imaging apparatus.

Before considering the present invention in more detail, some general background will be considered. Ultrasonic probes of the type described here generally include a transducer or transducing part embedded in or housed within a shielded plastic case or housing. Commonly, the ultrasonic imaging transducers that are used employ either a moving transducing element or an electronic scanning array transducer. In the first case, the transducer is moved to scan a surface while, in the second case, an acoustic propagation path is produced by electronically switching the transducer elements or aperture along the array. It is noted that this electronic scanning technique using a transducer array is well known to those skilled in the corresponding art so that further description thereof will be dispensed with. In all cases, the probes have a front face made of acoustically transparent material in order to not disturb the ultrasonic propagation. Otherwise, moving transducing devices require a specific coupling arrangement to operate.

Continuing the general description of the background of the invention, during a medical diagnosis using conventional ultrasonic imaging equipment the ultrasonic scanner is disposed in the vicinity of the operator and, therefore, the patient. The imaging probe is then positioned on the region of body to be imaged. Ultrasonic energy is transmitted and received through the transducer and the region to be diagnosed is generally displayed in sliced planes (a 1D image). The scanned section of organ is displayed in a gray scale image that is obtained by quantization of analog signals derived from returned echoes.

As indicated above, in actual operation, the scanning process is substantially more difficult and less effective to carry out than just described. Indeed, the ultrasonic waves emanating from the transducer are frequency bounded and subject to physical restraints of acoustic wave propagation. As a consequence, attenuation and impedance interface mismatches must be taken into account in the signal processing procedure. Accordingly, in order to display the image with equal contrast intensity, the imaging system must compensate for any attenuation of the frequency and amplitude of the signals travelling through the propagation medium. Therefore, frequency filters, and variable gain compensation techniques are used in processing the RF signals.

Others settings which are important in medical diagnosis are angle of view, the focus number and the depth of examination. Of course, control of most of these settings is provided by the system keyboard and this control may be effected by manipulation of various control buttons and/or trackball controls using scrolling menus. In practice, and in a manner designed to shorten the machine setup period, specific user diagnosis configurations are often stored in the system memory and then simply have to be loaded by the operator, so that, in normal use, only gain and focus controls are varied or adjusted during a diagnostic examination. However, depending on the morphology of the patient, the scanning area covered and the dynamic range must be adjusted during an examination to enhance the visual perception provided of the region of interest.

With this background, it would be appreciated that the provision of a pointing device such as a trackball or the like directly mounted on the ultrasonic probe will afford major gains in comfort and ease of use to the operator, who will now be able to easily and rapidly access these controls and, therefore, better attend to the patient. Using a single hand, the operator is capable of simultaneously selecting the scanning planes, controlling the gain of the image and modifying the settings for dynamic range or focus without any manipulation of the system keyboard. These features are of even greater significance as applied to endocavity probes (e.g., endorectal or endovaginal devices) and surgical imaging instruments such as endoscopes, laparoscopes or intravascular devices, where particular skill in manipulating the instruments is required. Moreover, the invention when applied to NDT transducers enables an expanded field of use of the instrument such as in severe environmental conditions or adverse temperature conditions, and when applied to ultrasonic probes for controlling another apparatus such as a therapy or drug delivery unit, provides added versatility. Further, an ultrasonic probe in accordance with the invention is advantageously equipped with a video output connector compatible with a RGB video output or a S-video output which can be plugged into a LCD display or an additional monitor, so that the probe is capable of operating remotely from its associated mainframe.

Before describing specific embodiments of the invention, the desirable characteristics of a suitable pointing device will be considered. It is to be understood that the pointing devices employed in accordance with the invention are preferably disposed on a main surface or face of the probe housing or case.

Although a trackball device may be used, this type of device is generally to be avoided because cleaning thereof is difficult (dust and dirt can contaminate the interstices between trackball and the casing so that sealed or otherwise completely covered devices are preferred for medical applications).

One pointing device that is particularly suitable for the purposes of the invention is a rocking key device such as that supplied by Fujitsu Takamisawa. The device is comprised of a small PCB (printed circuit board) on which are integrated a rocking key dome-type component and its associated electronic control circuits. This allows the device to be fitted to a digital controller to produce PS2 output similar to that of a conventional mouse. The dome-type pointing component is sealed and provides both ballistic and acceleration control. The device uses magnetic detection technology and thus requires no mechanical contact, thereby guaranteeing long life and reliability. Moreover, such a pointing device is compatible with the all direction (360°) control that is particularly advantageous in many of the applications of importance.

Another type of commercially available pointing device that is preferred for use in the present invention is the Digimouse device from Techtronic A/S (Denmark). This device is a miniature input device specially developed for handheld applications that require a navigation key to scroll in the menu presented on an associated screen or display. Without shifting between buttons, a user may scroll up and down the menu, jump left or right and select or enter his or her choice. Each of the scroll, left, right, and select functions provides tactile feedback. The MTBF is specified for more than 750,000 cycles. Further, the device can be integrated in a water tight manner in the probe housing or case.

Other pointing devices that can be used include a sensitive pad or a pointing button (similar to those used on a Notebook Computer), both of which are also available on the commercial market. It is noted that probes equipped with a sensitive pad are easier to clean or decontaminate because the pad has no prominent parts. However, a preferred embodiment includes the addition of a select or click button to complete the pointing device (it being noted that clicking on the sensitive pad and steering the probe can be a difficult task).

Referring to FIG. 1, there is shown a conventional commercially available imaging system. The system or apparatus, which is generally denoted 10, includes a pair of user interfaces 12 and 14 located at the mid-height of the system. In general, interface 12 comprises a keyboard and the interface 14 comprises a trackball and associated click buttons. Disposed below the keyboard 12 are plugs 16 which are adapted to be connected to imaging probes. A monitor display 18 is located at the upper portion of the system 10 and may be provided with color monitor compatible with the advanced imaging modes currently available (e.g., Doppler Color Flow Mapping (CFM), Power Doppler Imaging, and the like). The latest high-end ultrasound scanners are provided with Harmonic Imaging (HI) capabilities that significantly enhance perception of tissue contrast.

As indicated above, the present invention primarily relates to electronic scanning ultrasonic imaging systems and inherently to array transducers. However, the invention can be extended to any kind of transducer technology, such as moving sector or matrix without major changes. The system of the invention is provided with ultrasonic probes which act as a physical interface between the mainframe and the object of interest. In general, the probes can be represented as a black-box capable of transforming electrical energy into mechanical waves and vice versa, similarly to an antenna.

Figure 2:
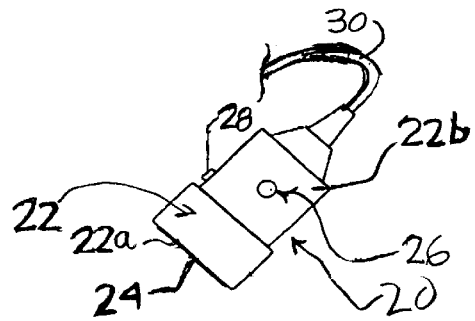
FIGS. 2 to 6 are front elevational views of ultrasonic probes in accordance with different preferred embodiments of the invention.

Referring to FIG. 2, there is depicted, in a schematic manner, an ultrasonic probe in accordance with a first embodiment of the invention. For purposes of simplicity, an external probe is shown and will be described. The probe, which is generally denoted 20, is composed of a plastic casing 26 having an opening located in the front face thereof wherein is mounted a transducer array 24. It will be appreciated that the shape of the opening varies depending on the type of transducer (linear or curved) which is used. FIG. 2 shows a linear transducer.

The probe housing or casing is formed by at least two sections 22a, 22b which are of different shapes and proportions. The transducer array 24 is housed or lodged in the section 22b so that this section is constructed based on the dimensions of the transducer array 24 and its associated components. On the other hand, section 22a is generally tailored to facilitate and improve assembly of the transducer arrangement. The housing section 22b is generally sized and spaced according to ergonomic considerations, and preferably should be of a smooth shape with bottleneck or other shaped portion in the region thereof adjacent the transducer section 22a. Inside section 22b are the interconnections connected between the transducer array 24 and the connecting cables so that the actual volume therein, and thus the size thereof, may be minimized by using low profile connectors or direct flex-cable soldering techniques (i.e., techniques wherein coaxial cables are soldered on tracks of flexible PCB so no connector is needed). In addition, the housing section 22b includes, at the other end thereof, an outwardly extending cable strain-relief portion through which a cable 30 passes.

In the preferred embodiment illustrated, on one of the main surfaces of section 22b a pointing device 26 is provided for controlling the imaging settings of the system. Pointing device 26 is electrically connected in parallel with the system trackball so as to be capable of identical operations. When pointing device 26 is further associated with a select button or click-button 28, the probe 20 is then capable of selecting and validating a number of functions of the imaging system, without user interfaces 12 and 14 of FIG. 1. For example, the probe 20 may be held by an operator in such a way that the thumb of the operator is placed on the pointing device 26 at the same time as the forefinger is placed on the validation or select button 28. It will be understood that this operation has no influence on the manipulation of the probe, and, indeed, will allow the operator to control the image setting in determining and tracking the best scanning position for diagnosis. This feature is particularly powerful in severe scanning conditions, such as, for instance, when investigating moving organs such as the myocardium or in blood flow investigations where the possibility of instantaneously freezing and/ or saving selected scanning planes of the implicated region will greatly improve the comfort level of the diagnosis made. Further, having control access to the system without having to move is similar to the advantages provided by the remote control IR unit of a television.

Figure 3:
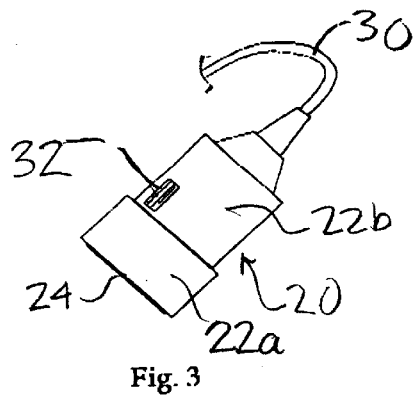

Referring to FIG. 3, a further embodiment of the probe is shown wherein like elements have been given the same reference numerals as in FIG. 1. This practice is also followed in subsequent drawings figures. In FIG. 3, the probe 20 is equipped with scrolling touch device 32 disposed on the main surface of the casing 22. The scrolling touch device 32 performs the same functions as the controls of FIG. 2. The probe 20 is held in the user's hand and the thumb or a finger is naturally placed on the scrolling touch device 32 to access the image controls. As in the embodiment of FIG. 2, the scrolling touch device 32 is connected in parallel with the user interface trackball of the system, and is capable of controlling the same functionalities. Unlike the static pointing device described in connection with FIG. 2, the scrolling touch device 32 requires the finger to perform more actions in order to generate the desired command. However, the device 32 is more suitable for use with system software that includes a scrolling menu.

Figure 4:
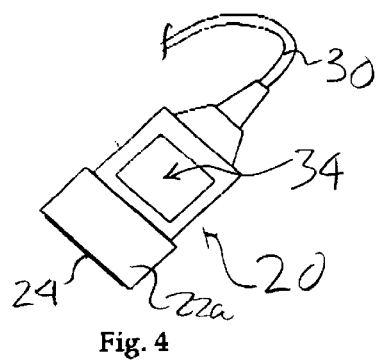

In the embodiment of FIG. 4, the pointing device comprises a planar touch sensitive pad 34, i.e., a device which is sensitive to contact by the fingers on the surface and wherein movement of a finger is automatically converted into displacement of a cursor (both respect to direction and displacement amplitude). It is important to note the absolute position of the cursor is not considered, but rather only the direction and displacement data is transmitted and interpreted by the system. Such sensitive touch pads, corresponding to pad 34, are based on capacitive detection and thus are more complex in construction than some other pointing devices and more fragile and so must be manipulated with care. A valid command can be entered by promptly contacting the surface of device 34, and a requirement for an additional validation touch can also be implemented if desired. One advantage of this embodiment is that the harmonious integration of the device 34 into the probe 20 results in a probe with pleasing visual appearance or cosmetic aspect.

Figure 5:
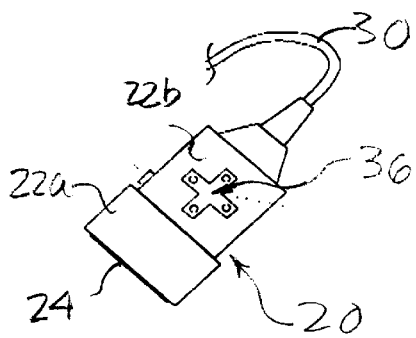

Referring to FIG. 5, the pointing device employed in this embodiment is a four direction steering device 36. Similarly to a Gamepad command device, the device 36 is articulated from a central point and a portion extending each cardinal direction may be touch activated independently, thereby enabling diagonal control of a cursor if two adjacent contact portions are simultaneously touch activated. The contact portions of device 36 are analog controlled so the amplitude of the contact force exerted thereon is proportional to the displacement speed of the cursor. This characteristic permits fine control of the direction of the cursor by exerting different pressures on the adjacent steering portions. The steering device 36 can be easily sealed under a conformable film or a protective flexible shell so that device 36 is compatible with medical use.

It will be apparent that FIGS. 2 to 5 depict ultrasonic probes with different pointing devices for controlling image settings by means of the cursor of system display. However, it will be understood that the invention is not limited to these embodiments.

Figure 6:
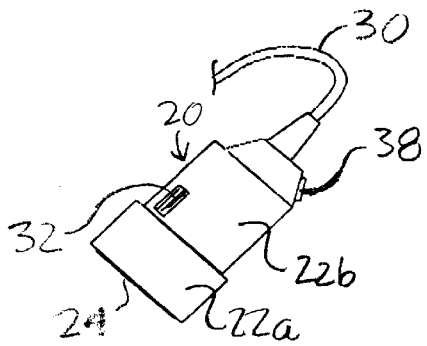
Figure 7:
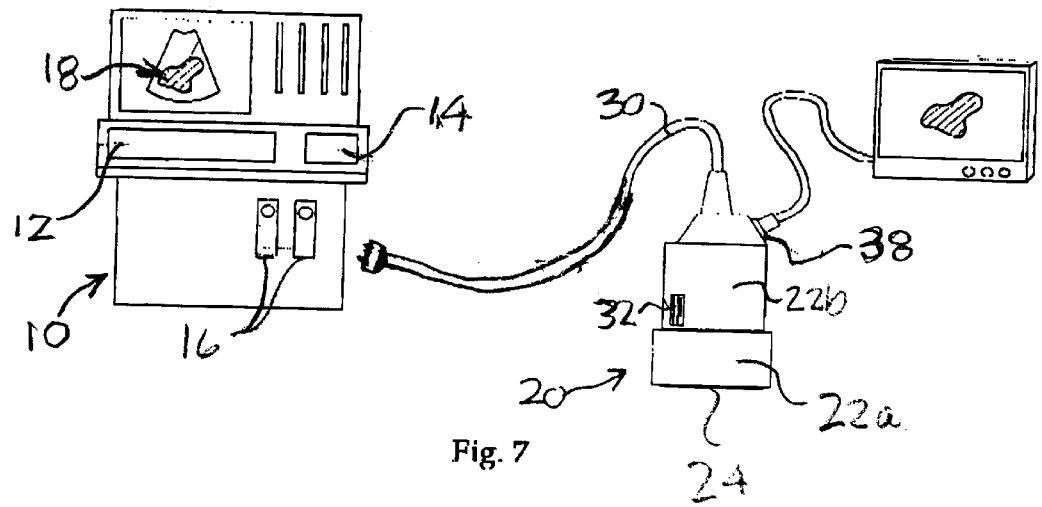
FIG. 7 is a front elevational view of the embodiment of FIG. 5 in use.

FIG. 6 shows an ultrasonic probe 2 which is similar to that of FIG. 3 but which is equipped with a video output connector 38 so as to enable the video display provided by the imaging system to be presented by another monitor that can be placed closer to the operator. This capability is particularly useful when applied to NDT applications where the region of inspection is in a restricted area in which the mainframe is not visible by the operator. The video output from connector 38 can be in RGB or S-Video format having NTSC or PAL standard so as to be compatible with a large variety of display monitors. In FIG. 7, the probe 20 of FIG. 6 is shown connected to a remote control monitor 40 that displays the same image as that visible on the monitor 18 of the system mainframe 10 (corresponding to that shown in FIG. 1). The other functions of the probe 20 of FIG. 7 are the same as described above.

Figure 8:
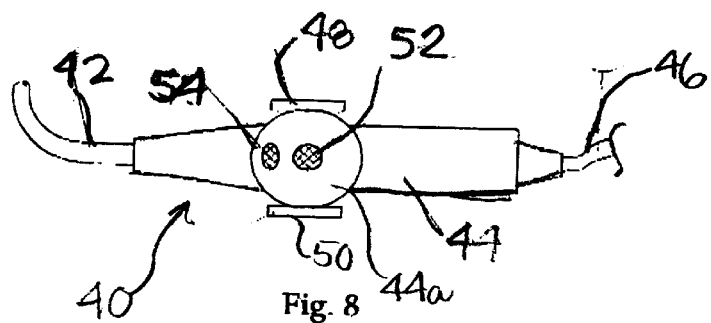
FIG. 8 is a side elevational view of yet another embodiment of the invention.

Referring to FIG. 8, a surgical imaging instrument 40 is shown which is equipped with remote imaging setting control capabilities as previously described. The instrument 40 depicted in FIG. 8 is an endoscopic probe but the invention can be employed in other types of instrument such as, e.g., laparoscopic probes. In FIG. 8, the instrument 40 is comprised of an elongated flexible hollow tube 42 (a rigid tube would be used in a laparoscope) having a plastic sheath and shielded with metallic braids. A handle 44 is affixed at one end thereof to the tube 42 and is connected to an output cable 46 at the other end thereof. A pair of steering control wheels 48 and 50 are mounted on a prominent or enlarged portion 44a of the handle 44 and are secured to steering cables (not shown) that pass through the tube 42 to be attached to a conventional bendable coupler (not shown) which is in turn assembled to the transducer tip (not shown).

A pointing device 52 and a select or validate button 54 are, in this embodiment, also located on the prominent portion 44a of the handle 44 at the vicinity of steering or control wheels 48 and 50.

With regard to the shape of the handle 44 and the location of the pointing device 52, it is first noted that a planar sensitive touch pad is not recommended for use as pointing device 52 because the very high level of sterilization required for such instrument makes a touch pad unsuitable. However, other types of pointing devices such as described previously can be used therein and can be placed either on the prominent portion 44a of handle 44 or can be placed on the cylindrical portion thereof without inconvenience. If desired, a sealed video output connector can be provided on the handle 44 for connection to an additional control monitor.

In an alternative embodiment, the pointing device and selector validate command device can be similarly provided on disposable imaging instruments such as those used in intravascular imaging or intracardiac imaging. More specifically, the invention is of particular value as applied to disposable instruments provided with a reusable steering control handle. The transducer and its associated inserting tube would be removed from the handle after use, and would be replaced by new sterile components for the next procedure. Thus, it is worthwhile implementing a pointing device on the handle in order to provide improved user comfort.

Figure 9:
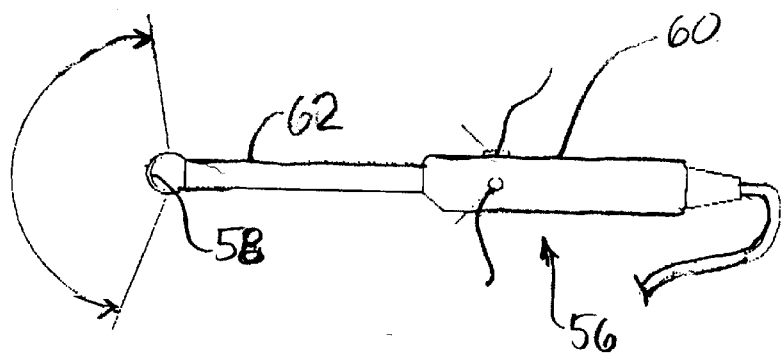
FIG. 9 is a side elevational view of a further embodiment of the invention.

Referring to FIG. 9, an endocavity imaging probe 56 is shown wherein a transducer element 58 is mounted at the distal tip of probe 56 and is typically of a curved shape designed to fit the anatomy of the organs to be imaged. The angle of view of transducer element 58 may be positioned according to the specificity of examination to be carried out and is thus variable. In general, the probe 56 comprises a substantially cylindrical handle 60 which is connected at one end to a smaller tubular portion 62 that is terminated by the transducer tip and is terminated at the other end by a cable 64 which extends outwardly therefrom. Handle 60 serves as a receptacle for the interconnections between the individual cables of cable 64 and the corresponding transducer connections (not shown) as well as to provide a support for biopsy attachment (not shown). The probe 56 is provided with a pointing device 66 and, optionally, a select or validate button 68, for controlling the image setting directly from the probe 56 without requiring the user to share his or her attention between the patient and the scanner. As previously described in connection with other embodiments, a video output connector can be provided on probe 56 for plugging the probe into an additional display monitor.

In the embodiments of the invention described above, the probe is equipped with a pointing device capable of duplicating certain functions of the scanner, thereby facilitating the examination of the patient. In other embodiments, the probe may also be provided with another further push button or other control devices for remote control of an additional apparatus or instruments such as patient treatment equipment or drug delivery equipment. This feature is of particular importance when the imaging probe is used to monitor treatment of an organ in that information concerning starting treatment can be transmitted by the imaging probe once the therapy equipment or instrument is properly positioned. In drug delivery, the transportation of capsules are detected by imaging transducer and compressing or collapsing of the drug dispensing envelope is controlled from the imaging probe by changing the ultrasonic power applied to the transducer.

Another aspect of the foregoing concerns protection of the quality of signal transmitted through the line. In this regard, as indicated above, ultrasonic waves are generated by electrical excitation of the piezoelectric transducer and reflections received from the medium travel along the same path prior to digital processing and display. Signals received from the probe have a large bandwidth so that these signals must be properly shielded against external noises and interferences. Typically, controlled impedance coaxial cables are used for signal transport and each coaxial cable is dedicated to an individual transducer. Shielding of these coaxial cables is achieved by connecting together all individual cable braids and the electrical ground for the system. This ground plane may be separate from the general ground associated with the system housing or casing. With regard to the present invention, it is preferable to separate the RF imaging information from the setting control data and the video channels (if any). Advantageously, the cable assembly should comprise a plurality of 50 ohm coaxial cables dedicated to RF information coming from and going to transducer, shielded video wires for video signals and further shielded twisted wires for transmitting control data. Further, in a preferred implementation, the cable assembly is sheathed overall by metallic braid insulated from wire shields and connected to the system housing or casing.

Although the invention has been described above in relation to preferred embodiments thereof, it will be understood by those skilled in the art that variations and modifications can be effected in these preferred embodiments without departing from the scope and spirit of the invention.

What is claimed:

1. An ultrasonic probe for use in diagnostic applications, said probe comprising:
    a probe housing;
    at least one ultrasonic transducer disposed in said housing;
    a plurality of cables disposed in a common sheath and connected to said probe housing;
    a pointing device mounted on said probe housing for controlling a plurality of functions of a remote imaging system associated with the probe and connected to said housing by said cables; and
    a video connector receptacle mounted on said probe housing for connection to an additional remote display which is separate from said remote imaging system and which is adapted to be located in the vicinity of an operator of the probe.

2. An ultrasonic probe according to claim 1 wherein the pointing device comprises a trackball device having an associated select function.

3. An ultrasonic probe according to claim 2 wherein said trackball device includes a select button.

4. An ultrasonic probe according to claim 1 wherein the pointing device comprises a rocking-key device having a select function.

5. An ultrasonic probe according to claim 1 wherein the pointing device comprises a scrolling device including a scrolling wheel wherein a cursor is controlled by scrolling the scrolling wheel and a select command is confirmed by pressure on the scrolling wheel.

6. An ultrasonic probe according to claim 1 wherein the pointing device comprises a touch-pad device mounted on a main surface of said probe housing.

7. An ultrasonic probe according to claim 6 wherein the touch-pad has a touch sensitive surface and converts movement of a finger of a user of the probe on the sensitive surface into cursor motion and wherein discrete pressure on the touch sensitive surface of the touch-pad is converted into a select command.

8. An ultrasonic probe according to claim 1 wherein said probe comprises an imaging instrument and said pointing device is mounted in a waterproof manner on said housing so that the imaging instrument is capable of controlling settings of the associated imaging system.

9. An ultrasonic probe according to claim 1 wherein said pointing device comprises a pointing and selecting device integrated into the probe housing for controlling functions of at least one of (i) an associated pulser/receiver and (ii) the associated imaging system.

10. An ultrasonic probe according to claim 1 wherein the probe is one of a flexible endoscopic type and a laparoscopic type.

11. An ultrasonic probe according to claim 1 wherein the probe is adapted to drive other apparatus used in conjunction with the imaging system.

12. An ultrasonic probe according to claim 1 wherein said probe includes a control button for directly controlling a power output mode of a driving system so as to be compatible with a drug delivery procedure.

13. An ultrasonic probe for use in diagnostic applications, said probe comprising:
    a housing including a distal tip and a proximal end;
    an ultrasonic transducer device mounted at the distal tip of the elongated housing;
    a control handle located at the proximal end of the housing;
    a cable output located on the handle; and
    a remote control pointing device located on the handle for controlling a plurality of functions of an associated imaging system and at least one further control member located on said handle for simultaneously controlling a drug delivery procedure.

14. An ultrasonic probe according to claim 13 wherein said housing comprises an elongated tubular instrument.

15. An ultrasonic probe according to claim 14 wherein the probe is of an endoscopic type and said instrument comprises a flexible elongated tube having a distal end and said transducer device is mounted at the distal end of the flexible tube.

16. An ultrasonic probe according to claim 14 wherein the probe is of a laparoscopic type and said instrument comprises a rigid elongated tube having a distal end and said transducer device is mounted at the distal end of the rigid tube.

17. An ultrasonic probe according to claim 14 wherein the probe comprises a disposable imaging device wherein the tubular instrument is removable from said control handle and said handle is equipped with said pointing device and extended connections.

18. An ultrasonic probe according to claim 14 wherein said probe comprises an imaging instrument and the said pointing device is mounted in a waterproof manner on the handle of the imaging instrument so that the instrument is capable of controlling associated imaging system settings.

19. An ultrasonic probe according to claim 13 wherein said pointing device comprises a pointing and selecting device integrated into said control handle for controlling functions of at least one of (i) an associated pulser/receiver and (ii) the associated imaging system.

20. An ultrasonic probe according to claim 19 wherein the probe handle includes a video connector receptacle for connection to an additional remote control display located in the vicinity of an operator of the probe.

21. An ultrasonic probe according to claim 13 wherein the probe is one of (i) a flexible endoscopic type and (ii) a laparoscopic type.

22. An ultrasonic probe for use in diagnostic applications, said probe comprising:
    a probe housing;
    at least one ultrasonic transducer disposed in said housing;

a plurality of cables disposed in a common sheath and connected to said probe housing; and a pointing device mounted on said probe housing for controlling a plurality of functions of a remote imaging system associated with the probe and connected to said housing by said cable, said imaging system providing a plurality of different imaging modes including a harmonic imaging mode, and said pointing device enabling switching between said modes.

* * * * *